(12) United States Patent
Wollenberg et al.

(10) Patent No.: US 7,462,490 B2
(45) Date of Patent: Dec. 9, 2008

(54) COMBINATORIAL LUBRICATING OIL COMPOSITION LIBRARIES

(75) Inventors: Robert H. Wollenberg, Orinda, CA (US); Thomas J. Balk, San Francisco, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 32 days.

(21) Appl. No.: 10/699,529

(22) Filed: Oct. 31, 2003

(65) Prior Publication Data

US 2005/0095718 A1    May 5, 2005

(51) Int. Cl.
*G01N 33/26* (2006.01)

(52) U.S. Cl. .............................. 436/60; 436/55; 506/13; 506/22; 506/23; 508/110

(58) Field of Classification Search .................... 436/60, 436/55; 422/61–63, 67, 68.1; 252/408.1; 435/DIG. 1, DIG. 22, DIG. 29, DIG. 46, 435/DIG. 49; 508/110; 506/13, 22, 23
See application file for complete search history.

(56) References Cited

U.S. PATENT DOCUMENTS

| | | | |
|---|---|---|---|
| 5,959,297 A | 9/1999 | Weinberg et al. | |
| 5,985,356 A | 11/1999 | Schultz et al. | |
| 6,004,617 A | 12/1999 | Schultz et al. | |
| 6,030,917 A | 2/2000 | Weinberg et al. | |
| 6,034,775 A | 3/2000 | McFarland et al. | |
| 6,045,671 A | 4/2000 | Wu et al. | |
| 6,087,181 A | 7/2000 | Cong | |
| 6,149,882 A | 11/2000 | Guan et al. | |
| 6,157,449 A | 12/2000 | Hajduk | |
| 6,175,409 B1 | 1/2001 | Nielsen et al. | |
| 6,182,499 B1 | 2/2001 | McFarland et al. | |
| 6,187,164 B1 | 2/2001 | Warren et al. | |
| 6,248,540 B1 | 6/2001 | Weinberg et al. | |
| 6,260,407 B1 | 7/2001 | Petro et al. | |
| 6,265,226 B1 | 7/2001 | Petro et al. | |
| 6,296,771 B1 | 10/2001 | Miroslav | |
| 6,326,090 B1 | 12/2001 | Schultz et al. | |
| 6,336,353 B2 | 1/2002 | Matsiev et al. | |
| 6,345,528 B2 | 2/2002 | Petro et al. | |
| 6,346,290 B1 | 2/2002 | Schultz et al. | |
| 6,371,640 B1 | 4/2002 | Hajduk et al. | |
| 6,373,570 B1 | 4/2002 | McFarland et al. | |
| 6,393,895 B1 | 5/2002 | Matsiev et al. | |
| 6,393,898 B1 | 5/2002 | Hajduk et al. | |

(Continued)

FOREIGN PATENT DOCUMENTS

EP    1233361    *    8/2002

(Continued)

OTHER PUBLICATIONS

The Condensed Chemical Dictionary, tenth edition, 1981, p. 20.*

*Primary Examiner*—Maureen M Wallenhorst
(74) *Attorney, Agent, or Firm*—Claud J. Caroll; M. Carmen & Associates, PLLC

(57) ABSTRACT

A combinatorial lubricating oil composition library is provided including at least a plurality of different lubricating oil compositions comprising (a) a major amount of a base oil of lubricating viscosity and (b) at least one lubricating oil additive. Methods for preparing same are also provided.

25 Claims, 8 Drawing Sheets

U.S. PATENT DOCUMENTS

| | | | |
|---|---|---|---|
| 6,395,552 | B1 | 5/2002 | Borade et al. |
| 6,401,519 | B1 | 6/2002 | McFarland et al. |
| 6,406,632 | B1 | 6/2002 | Safir et al. |
| 6,410,331 | B1 | 6/2002 | Schultz et al. |
| 6,419,881 | B1 | 7/2002 | Weinberg et al. |
| 6,420,179 | B1 | 7/2002 | Schultz et al. |
| 6,436,292 | B1 | 8/2002 | Petro |
| 6,438,497 | B1 | 8/2002 | Mansky et al. |
| 6,440,745 | B1 | 8/2002 | Weinberg et al. |
| 6,441,901 | B2 | 8/2002 | McFarland et al. |
| 6,461,515 | B1 | 10/2002 | Safir et al. |
| 6,468,806 | B1 | 10/2002 | McFarland et al. |
| 6,475,391 | B2 | 11/2002 | Safir et al. |
| 6,484,567 | B1 | 11/2002 | Hajduk et al. |
| 6,491,816 | B2 | 12/2002 | Petro |
| 6,508,984 | B1 | 1/2003 | Turner et al. |
| 6,519,032 | B1 | 2/2003 | Kuebler et al. |
| 6,528,026 | B2 | 3/2003 | Hajduk et al. |
| 6,535,284 | B1 | 3/2003 | Hajduk et al. |
| 6,535,824 | B1 | 3/2003 | Mansky et al. |
| 6,536,944 | B1 | 3/2003 | Archibald et al. |
| 6,541,271 | B1 | 4/2003 | McFarland et al. |
| 6,553,318 | B2 | 4/2003 | Mansky |
| 6,576,906 | B1 | 6/2003 | Archibald et al. |
| 6,577,392 | B1 | 6/2003 | Nielsen et al. |
| 6,582,116 | B2 | 6/2003 | Nielsen |
| 6,605,473 | B1 | 8/2003 | Hajduk et al. |
| 6,644,101 | B2 | 11/2003 | Hajduk et al. |
| 6,649,413 | B1 | 11/2003 | Schultz et al. |
| 6,650,102 | B2 | 11/2003 | Hajduk et al. |
| 6,653,138 | B1 | 11/2003 | Turner et al. |
| 6,655,194 | B2 | 12/2003 | Hajduk et al. |
| 6,658,429 | B2 | 12/2003 | Dorsett, Jr. |
| 6,664,067 | B1 | 12/2003 | Hajduk et al. |
| 6,668,622 | B2 | 12/2003 | Hajduk et al. |
| 6,670,298 | B1 | 12/2003 | Weinberg et al. |
| 6,679,130 | B2 | 1/2004 | Hajduk et al. |
| 6,681,618 | B2 | 1/2004 | Hajduk et al. |
| 6,686,205 | B1 | 2/2004 | Schultz et al. |
| 6,690,179 | B2 | 2/2004 | Hajduk et al. |
| 2002/0023507 | A1 | 2/2002 | Hahduk et al. |
| 2002/0028456 | A1 | 3/2002 | Manksy et al. |
| 2002/0029621 | A1 | 3/2002 | Hajduk et al. |
| 2002/0032531 | A1 | 3/2002 | Mansky et al. |
| 2002/0098332 | A1 | 7/2002 | Warren et al. |
| 2002/0148282 | A1 | 10/2002 | Hajduk et al. |
| 2002/0155036 | A1 | 10/2002 | Hajduk et al. |
| 2002/0164275 | A1 | 11/2002 | Wheeler et al. |
| 2003/0007152 | A1 | 1/2003 | McFarland et al. |
| 2003/0032198 | A1 | 2/2003 | Lugmair et al. |
| 2003/0032205 | A1 | 2/2003 | McFarland et al. |
| 2003/0037601 | A1 | 2/2003 | Manksy et al. |
| 2003/0037620 | A1 | 2/2003 | Mansky |
| 2003/0041653 | A1 | 3/2003 | Matsiev et al. |
| 2003/0041671 | A1 | 3/2003 | Hajduk et al. |
| 2003/0041672 | A1 | 3/2003 | Hajduk et al. |
| 2003/0041676 | A1 | 3/2003 | Hajduk et al. |
| 2003/0054740 | A1 | 3/2003 | Mansky |
| 2003/0055587 | A1 | 3/2003 | Wang et al. |
| 2003/0056576 | A1 | 3/2003 | Mansky |
| 2003/0068829 | A1 | 4/2003 | Giaquinta et al. |
| 2003/0097871 | A1 | 5/2003 | Mansky |
| 2003/0100119 | A1 | 5/2003 | Weinberg et al. |
| 2003/0127776 | A1 | 7/2003 | Carlson et al. |
| 2003/0133113 | A1 | 7/2003 | Hajduk et al. |
| 2003/0138025 | A1 | 7/2003 | Archibald et al. |
| 2003/0141613 | A1 | 7/2003 | Hajduk et al. |
| 2003/0142309 | A1 | 7/2003 | Kuebler et al. |
| 2003/0157721 | A1 | 8/2003 | Turner et al. |
| 2003/0161763 | A1 | 8/2003 | Erden et al. |
| 2003/0169638 | A1 | 9/2003 | Nielsen |
| 2003/0190260 | A1 | 10/2003 | Wheeler et al. |
| 2003/0203500 | A1 | 10/2003 | Carlson et al. |
| 2003/0211016 | A1 | 11/2003 | Dales et al. |
| 2003/0218467 | A1 | 11/2003 | Carlson et al. |
| 2003/0219906 | A1 | 11/2003 | Giaquiinta et al. |
| 2004/0123650 | A1 * | 7/2004 | Kolosov et al. ............. 73/54.28 |
| 2004/0144355 | A1 * | 7/2004 | Carey et al. ............. 123/196 R |

FOREIGN PATENT DOCUMENTS

| | | | |
|---|---|---|---|
| WO | 95/13538 | * | 5/1995 |
| WO | 02/07870 | * | 1/2002 |

* cited by examiner

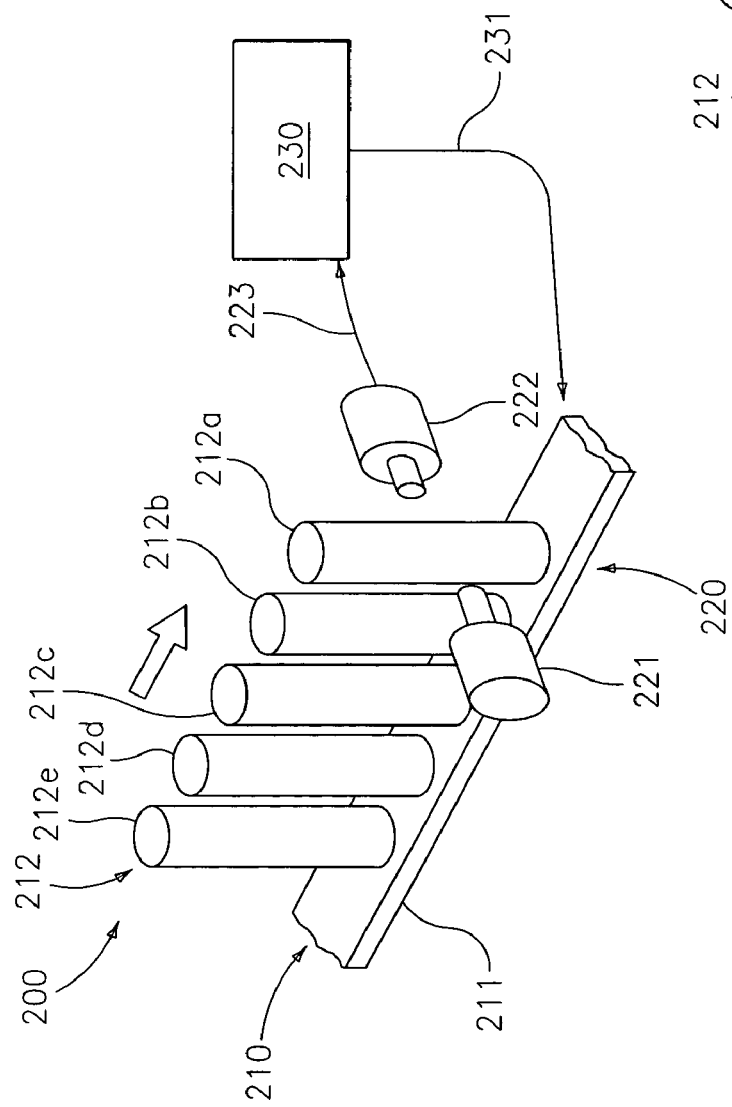
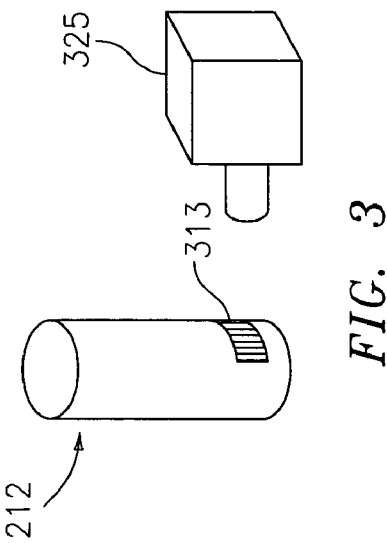
FIG. 2
FIG. 3

COMBINATORIAL LUBRICATING OIL COMPOSITION LIBRARIES

BACKGROUND OF THE INVENTION

1. Technical Field

The present invention relates generally to combinatorial lubricating oil composition libraries.

2. Description of the Related Art

The use of a combinatorial approach for materials synthesis is a relatively new area of research aimed at using rapid synthesis and screening methods to build libraries of polymeric, inorganic or solid state materials. For example, advances in reactor technology have empowered chemists and engineers to rapidly produce large libraries of discrete organic molecules in the pursuit of new drug discovery, which have led to the development of a growing branch of research called combinatorial chemistry. Combinatorial chemistry generally refers to methods and materials for creating collections of diverse materials or compounds—commonly known as libraries—and to techniques and instruments for evaluating or screening libraries for desirable properties.

Presently, research in the lubricant industry involves individually forming candidate lubricating oil compositions and then performing a macro-scale analysis of the candidate compositions by employing a large amount of the candidate to be tested. Additionally, the methods employed for testing each candidate composition require manual operation. This, in turn, significantly reduces the number of compositions that can be tested and identified as leading lubricating oil compositions.

Drawbacks associated with conventional screening procedures can be seen as follows. For example, governmental and automotive industry pressure towards reducing the phosphorous and sulfur content of lubricating oil compositions used as, for example, passenger car and heavy duty diesel engine oils, is leading to new research to identify oil compositions which can satisfy certain tests such as, for example, oxidation, wear and compatibility tests, while containing low levels of phosphorous and sulfur. In this context, United States Military Standards MIL-L-46152E and the ILSAC Standards defined by the Japanese and United States Automobile Industry Association at present require the phosphorous content of engine oils to be at or below 0.10 wt. % with future phosphorous content being proposed to even lower levels, e.g., 0.08 wt. % by January, 2004 and below 0.05 wt. % by January, 2006. Also, at present, there is no industry standard requirement for sulfur content in engine oils, but it has been proposed that the sulfur content be below 0.2 wt. % by January, 2006. Thus, it would be desirable to decrease the amount of phosphorous and sulfur in lubricating oils still further, thereby meeting future industry standard proposed phosphorous and sulfur contents in the engine oil while still retaining the oxidation or corrosion inhibiting properties and antiwear properties of the higher phosphorous and sulfur content engine oils. In order to accomplish this, a large number of proposed lubricating oil compositions must be tested to determine which compositions may be useful.

Additionally, similar changes in specifications and changing customer needs also drive reformulation efforts in other lubricant applications such as, for example, transmission fluids, hydraulic fluids, gear oils, marine cylinder oils, compressor oils, refrigeration lubricants and the like.

However, as stated above, present research in the lubricant industry does not allow for reformulation to occur in an expeditious manner. As such, there exists a need in the art for a more efficient, economical and systematic approach for the preparation of lubricating oil compositions and screening of such compositions for information correlating to the actual useful properties of the compositions.

Accordingly, it would be desirable to formulate a large number of different candidate lubricating oil compositions and then rapidly test a plurality of sample candidates utilizing small amounts of each sample. In this manner, a vast number of diverse compositions can be timely evaluated and characterized to identify leading lubricating oil compositions. Additionally, it would be desirable to provide combinatorial lubricating oil composition libraries containing information related to each of the tested lubricating oil compositions which can be used to select lubricating oil compositions according to the properties desired by the end user.

SUMMARY OF THE INVENTION

In accordance with the present invention, a combinatorial lubricating oil composition library is provided comprising a plurality of different lubricating oil compositions comprising (a) a major amount of a base oil of lubricating viscosity and (b) at least one lubricating oil additive.

In a second embodiment of the present invention, a method for producing a combinatorial lubricating oil composition library is provided comprising (a) providing a library of a plurality of different lubricating oil composition samples comprising (i) a major amount of at least one base oil of lubricating viscosity and (ii) a minor amount of at least one lubricating oil additive, each sample being in a respective one of a plurality of test receptacles; (b) measuring lubricating oil composition properties of each sample to provide the lubricating oil composition property data for each sample; and, (c) outputting the results of step (b).

BRIEF DESCRIPTION OF THE DRAWINGS

Various embodiments are described below with reference to the drawings wherein:

FIG. 2 is a schematic diagram of a system for measuring storage stability of a plurality of samples of different lubricating oil additive compositions and/or lubricating oil compositions;

FIG. 3 illustrates a test receptacle having a bar code in conjunction with a bar code reader; and, FIG. 4 is a schematic diagram of a system using a robotic assembly for individually retrieving test receptacles;

DETAILED DESCRIPTION OF THE PREFERRED EMBODIMENTS

Figure 1:
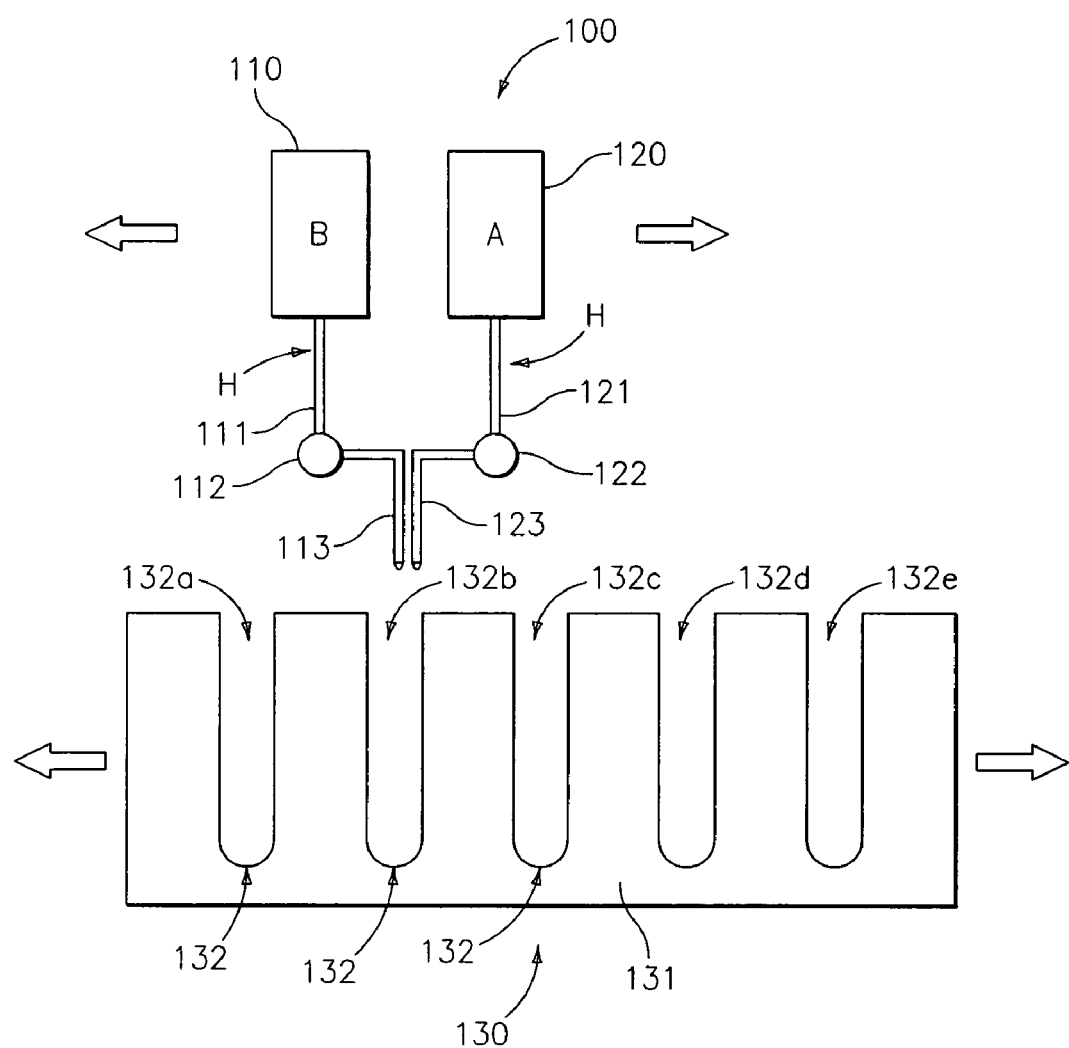
FIG. 1 is a schematic diagram of a system for preparing a plurality of different lubricating oil compositions.

In accordance with the present invention, a combinatorial lubricating oil composition library is provided comprising a plurality of different lubricating oil compositions comprising (a) a major amount of a base oil of lubricating viscosity and (b) at least one lubricating oil additive. As used herein, a combinatorial library is an intentionally created collection of a plurality of differing molecules which can be prepared by selected means and screened for a desired property or characteristic in a variety of formats (e.g., libraries of lubricating oil additive formulations, libraries of lubricating oil composition formulations, libraries of subsets of lubricating oil additive formulations or lubricating oil composition formulations, libraries of storage stability data, etc.). The libraries are generally prepared such that the compounds are in varying quantities. Screening methods for libraries vary greatly and are dependent upon a desired property or characteristic, the size of library, and the class of compounds in the library.

The libraries of the instant invention can be of any type. These types include, but are not limited to, mixtures. Mixture libraries ordinarily contain a mixture of compounds that are simultaneously formulated and assayed. Identification of the most active compound is then performed by screening the mixtures.

The library of the present invention is provided by a high throughput preparation and screening method for determining lubricant performance of a plurality of different lubricating oil compositions by subjecting a plurality of different lubricating oil composition samples in a respective one of a plurality of test receptacles to measure, for example, storage stability, oxidation stability and antiwear properties. The expression "high throughput" as used herein shall be understood to mean that a diverse number of different lubricating oil compositions are rapidly prepared and analyzed. In a first step in forming the library of the present invention, varying quantities of at least one base oil of lubricating viscosity and at least one lubricating oil additive are introduced in respective test reservoirs so that each reservoir contains a different lubricating oil composition having a different composition depending upon the percentage amounts and/or types of the additives combined with the base oil of lubricating viscosity in each receptacle. Data regarding the composition of each sample are stored in a data library. The procedure is advantageously accomplished under program control and is automatically controlled by, for example, a microprocessor or other computer control device. The expression "program control" as used herein shall be understood to mean the equipment used herein in providing the plurality of lubricating oil compositions is automated and controlled by computer control.

The lubricating oil compositions in the library of this invention include as a first component a major amount of base oil of lubricating viscosity, e.g., an amount of greater than 50 wt. %, preferably greater than about 70 wt. %, more preferably from about 80 to about 99.5 wt. % and most preferably from about 85 to about 98 wt. %, based on the total weight of the composition. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered base oil of lubricating viscosity used in formulating lubricating oil compositions for any and all such applications, e.g., engine oils, marine cylinder oils, functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60,5W, 5W-20,5W-30, 5W-40,5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fischer-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The second component of the lubricating oil compositions for use herein is at least one lubricating oil additive. Such additives can be any presently known or later-discovered additive used in formulating lubricating oil compositions. The lubricating oil additives for use herein include, but are not limited to, antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. Greases will require the addition of appropriate thickeners. A variety of the additives are known and commercially available. These additives, or their analogous compounds, can be employed for the preparation of the various lubricating oil compositions herein.

Alternatively, the lubricating oil additive(s) can further contain a diluent oil to form an additive concentrate. These concentrates usually include at least from about 90 wt. % to about 10 wt. % and preferably from about 90 wt. % to about 50 wt. %, of a diluent oil and from about 10 wt. % to about 90 wt. %, preferably from about 10 wt. % to about 50 wt. %, of the foregoing additive(s). Suitable diluents for the concentrates include any inert diluent, preferably an oil of lubricating viscosity such as, for example, a base oil as described hereinbelow, so that the concentrate may be readily mixed with lubricating oils to prepare lubricating oil compositions. Suitable lubricating oils that may be used as diluents can be any oil of lubricating viscosity.

Generally the lubricating oil compositions of the present invention will include at least one antioxidant. Examples of antioxidants include, but are not limited to, hindered phenolic antioxidants, secondary aromatic amine antioxidants, sulfurized phenolic antioxidants, oil-soluble copper compounds, phosphorus-containing antioxidants, organic sulfides, disulfides and polysulfides and the like. The antioxidants will ordinarily be present in the lubricating oil compositions of the present invention at a concentration ranging from about 0.1 to about 5 weight percent.

Examples of sterically hindered phenolic antioxidants include, but are not limited to, ortho-alkylated phenolic compounds such as 2,6-di-tertbutylphenol, 4-methyl-2,6-di-tert-butylphenol, 2,4,6-tri-tertbutylphenol, 2-tert-butylphenol, 2,6-diisopropylphenol, 2-methyl-6-tert-butylphenol, 2,4-dimethyl-6-tert-butylphenol, 4-(N,N-dimethylaminomethyl)-2,6-di-tertbutyl phenol, 4-ethyl-2,6-di-tertbutylphenol, 2-methyl-6-styrylphenol, 2,6-distyryl-4-nonylphenol, and their analogs and homologs. Mixtures of two or more such mononuclear phenolic compounds are also suitable.

Examples of other phenol antioxidants for use in the lubricating oil compositions of the present invention include, but are not limited to, methylene-one or more of bridged alkylphenols, one or more sterically-hindered unbridged phenolic compounds and mixtures thereof. Examples of methylene-bridged compounds include, but are not limited to, 4,4'-methylenebis(6-tert-butyl o-cresol), 4,4'-methylenebis(2-tert-amyl-o-cresol), 2,2'-methylenebis(4-methyl-6-tert-butylphenol), 4,4'-methylene-bis(2,6-di-tertbutylphenol), and the like. Particularly preferred are mixtures of methylene-bridged alkylphenols such as those described in U.S. Pat. No. 3,211,652, the contents of which are incorporated by reference herein.

Amine antioxidants can also be used in the lubricating oil compositions of this invention. Examples include, but are not limited to, oil-soluble aromatic secondary amines, aromatic secondary polyamines and the like and combinations thereof with aromatic secondary amines being preferred. Examples of aromatic secondary monoamines include diphenylamine, alkyl diphenylamines containing 1 or 2 alkyl substituents each having up to about 16 carbon atoms, phenyl-alpha-naphthylamine, phenyl-beta-napthylamine, alkyl- or aralkyl-substituted phenyl-alpha-naphthylamine containing at least one or two alkyl or aralkyl groups each having up to about 16 carbon atoms, alkyl- or aralkyl-substituted phenyl-beta-naphthylamine containing at least one or two alkyl or aralkyl groups each having up to about 16 carbon atoms, and the like.

A preferred type of aromatic amine antioxidant is an alkylated diphenylamine of the general formula

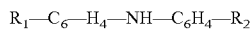

$$R_1—C_6—H_4—NH—C_6H_4—R_2$$

wherein $R_1$ is an alkyl group (preferably a branched alkyl group) having 6 to 12 carbon atoms and preferably 8 or 9 carbon atoms; and $R_2$ is a hydrogen atom or an alkyl group (preferably a branched alkyl group) having 6 to 12 carbon atoms and preferably 8 or 9 carbon atoms. Most preferably, $R_1$ and $R_2$ are the same. One such preferred compound is available commercially as Naugalube 438L, a material which is understood to be predominately a 4,4'-dinonyldiphenylamine (i.e., bis(4-nonylphenyl)(amine) wherein the nonyl groups are branched.

Another antioxidant for use in the lubricating oil compositions of this invention is comprised of one or more liquid, partially sulfurized phenolic compounds such as those prepared by reacting sulfur monochloride with a liquid mixture of phenols wherein at least about 50 weight percent of the mixture of phenols is composed of one or more reactive, hindered phenols and in proportions to provide from about 0.3 to about 0.7 gram atoms of sulfur monochloride per mole of reactive, hindered phenol so as to produce a liquid product. Typical phenol mixtures useful in making such liquid product compositions include a mixture containing by weight about 75% of 2,6-di-tert-butylphenol, about 10% of 2-tert-butylphenol, about 13% of 2,4,6-tri-tertbutylphenol, and about 2% of 2,4-di-tertbutylphenol. The reaction is exothermic and is preferably kept within the range of about 15° C. to about 70° C., most preferably between about 40° C. to about 60° C.

Mixtures of different antioxidants can also be used in the lubricating oil compositions of the present invention. One suitable mixture is comprised of a combination of (i) an oil-soluble mixture of at least three different sterically-hindered tertiary butylated monohydric phenols which is in the liquid state at 25° C., (ii) an oil-soluble mixture of at least three different sterically-hindered tertiary butylated methylene-bridged polyphenols, and (iii) at least one bis(4-alkylphenyl) amine wherein the alkyl group is a branched alkyl group having 8 to 12 carbon atoms, the proportions of (i), (ii) and (iii) on a weight basis falling in the range of about 3.5 to about 5.0 parts of component (i) and about 0.9 to about 1.2 parts of component (ii) per part by weight of component (iii). Examples of such antioxidants discussion above are disclosed in U.S. Pat. No. 5,328,619, the contents of which are incorporated by reference herein. Other useful antioxidants are those disclosed in U.S. Pat. No. 4,031,023, the contents of which are incorporated by reference herein.

Examples of antioxidants include, but are not limited to, aminic types, e.g., diphenylamine, phenyl-alpha-napthyl-amine, N,N-di(alkylphenyl) amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic) phenol; sulfur-containing materials, e.g., sulfurized olefins or esters and the like and mixtures thereof.

Examples of antiwear agents include, but are not limited to, zinc dialkyldithiophosphates and zinc diaryldithiophosphates, e.g., those described in an article by Born et al. entitled "Relationship between Chemical Structure and Effectiveness of Some Metallic Dialkyl- and Diaryl-dithiophosphates in Different Lubricated Mechanisms", appearing in Lubrication Science 4-2 January 1992, see for example pages 97-100; aryl phosphates and phosphites, sulfur-containing esters, phosphosulfur compounds, metal or ash-free dithiocarbamates, xanthates, alkyl sulfides and the like and mixtures thereof.

Examples of detergents include, but are not limited to, overbased or neutral detergents such as sulfonate detergents, e.g., those made from alkyl benzene and fuming sulfuric acid; phenates (high overbased or low overbased), high overbased phenate stearates, phenolates, salicylates, phosphonates, thiophosphonates, ionic surfactants and the like and mixtures thereof. Low overbased metal sulfonates typically have a total base number (TBN) of from about 0 to about 30 and preferably from about 10 to about 25. Low overbased metal sulfonates and neutral metal sulfonates are well known in the art.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine, e.g., those disclosed in U.S. Ser. No. 10/402,170, filed Mar. 28, 2003, the contents of which are incorporated by reference herein, and the like and mixtures thereof.

Examples of antifoaming agents include, but are not limited to, polymers of alkyl methacrylate; polymers of dimethylsilicone and the like and mixtures thereof.

Examples of ashless dispersants include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, phosphonoamides, thiophosphonamides and phosphoramides; thiazoles, e.g., 2,5-dimercapto-1,3,4-thiadiazoles, mercaptobenzothiazoles and derivatives thereof; triazoles, e.g., alkyltriazoles and benzotriazoles; copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof. The derivatives of these dispersants, e.g., borated dispersants such as borated succinimides, may also be used. Preferably, the dispersants are polyalkylene succinimides derived from animation of polyalkylene succinic anhydrides with polyalkylene polyamine.

If desired, prior to dispensing the at least one base oil and at least one lubricating oil additive to provide the compositions herein, as discussed hereinbelow, it can be advantageous to conduct molecular modeling of proposed compounds for use in the compositions (i.e., formulations) to determine which compounds may provide potential leading candidate compositions. For example, calculations can be carried out involving such factors as, for example, transition states, bond lengths, bond angles, dipole moment, hydrophobicity, etc, of the compounds. Accordingly, the proposed compounds can be screened to determine, for example, which compounds may perform poorly in an oxidation inhibition process due to a poor ability to trap intermediate peroxides. This can be carried out using known software such as, for example, Quantum Mechanics available from Accelrys (San Diego, Calif.).

Software for the design of test libraries can be used to design the original compound test libraries based on input from the foregoing experimental program(s). This software can be used to efficiently design test libraries that cover the desired experimental space and utilize statistical experimental design methods. Other software can then be used to analyze the data from the experiments and correlate that data with the structure of the compounds and/or compound treatment conditions and/or reaction conditions. Such correlations are often referred to as QSAR software (Quantitative Structure Activity Relations) available from Accelrys (San Diego, Calif.). Such QSAR programs can then be used by the software to design subsequent compound test libraries for further screening.

The use of such QSAR programs can add to the efficiency of screening. As more data is collected, these QSAR programs can become more efficient at developing compound libraries with increased probability for finding desirable compounds. For example, the compounds analyzed can be formulated into various lubricating oil compositions, as described hereinbelow, and then further analyzed by way of, for example, regression and analysis technologies, using known software, e.g., $C^2$-QSAR available from Accelrys (San Diego, Calif.). In this manner, validation of the data obtained from the molecular modeling can be achieved and then this data can also be stored in a data collector. In this way, new compounds, conceived by one skilled in the art can be checked by the QSAR software to predict their activity prior to their actual synthesis. Additionally, such software tools may be utilized to prioritize a list of possible compounds being considered for synthesis in such a way that one skilled in the art will have a higher probability for success.

Referring now to FIG. 1, an example of a system to provide the foregoing compositions in the plurality of respective test receptacles is generally illustrated as system 100. Representative of this system and method for providing the foregoing compositions in the plurality of respective test receptacles is one disclosed in co-pending U.S. patent application Ser. No. 10/699,510 filed on Oct. 31, 2003 and entitled "HIGH THROUGHPUT PREPARATION OF LUBRICATING OIL COMPOSITIONS FOR COMBINATORIAL LIBRARIES" by Wollenberg et al. and having a common assignee with the present application, the contents of which are incorporated by reference herein. Generally, vessel 110 contains a supply of the foregoing base oils of lubricating viscosity B. Vessel 120 contains a supply of additive A, which can be any of the foregoing additives useful for modifying the properties of the base oil. As one skilled in the art would readily appreciate, one or more of vessels 110 and vessels 120 can be used when dispensing more than one base oil and/or more than one additive, respectively.

Tubular line 111 is a conduit for communicating the base oil B to nozzle portion 113, from which it can be dispensed into a selected test reservoir, as described below. The amount of base oil dispensed is determined by metering pump 112, which can be computer controlled.

Tubular line 121 is a conduit for communicating the lubricating oil additive A to nozzle portion 123, from which it can be dispensed into a selected test reservoir, as described below. The amount of lubricating oil additive dispensed is determined by metering pump 122, which also can be computer controlled. Computer programs and systems for automatically metering predetermined amounts of materials in accordance with a preselected protocol are known in the art and can be used herein.

Nozzles 113 and 123 are preferably in close proximity so that base oil B and additive A can be simultaneously dispensed in a test reservoir. Alternatively, base oil B and additive A can be sequentially added to the test reservoir. The nozzles 113 and 123 can comprise a multichannel pipette or one or more syringe needles.

The vessels 110 and 120 can be under pressure. Optionally, more than two vessels can be employed. Metering pumps suitable for use in the invention are known and commercially available. In the event that highly viscous lubricant base stock or additives are used, the vessels 110 and 120 and/or the tubular lines 111 and 121, metering pumps 112 and 122, and/or nozzles 113 and 123 can be heated to facilitate fluid flow therethrough.

The test frame 130 includes a block 131 of transparent material (e.g., glass) having a plurality of recesses 132 for receiving the dispensed additives or base oil and additives. The recesses provide test reservoirs wherein each reservoir contains lubricating oil compositions of a different and predetermined composition, i.e., the percentage and/or type of base oil and/or additives in each composition will vary from one reservoir to another. Optionally, the reservoirs can be individual receptacles (e.g., test tubes) mounted upon a rack, instead of being recesses in a block. Preferably, the test receptacles comprise transparent glass tubes. While five reservoirs, i.e., recesses 132a, 132b, 132c, 132d, 132e, are illustrated in FIG. 1, any number of reservoirs can be employed herein. For example the system can employ 20, 50, 100 or even more test receptacles and samples as required.

The individual reservoirs are adapted to hold relatively small amounts of lubricating oil samples. The sample size in each reservoir can generally be no more than about 20 ml, preferably no more than about 15 ml, more preferably no more than about 10 ml and yet more preferably no more than about 5 ml.

The test frame 130 and dispensing nozzles 113 and 123 are movable relative to one another. Although manual movement of the apparatus by an equipment operator is within the purview of the invention, robotic mechanisms with programmable movement are preferred. In one embodiment the test frame 130 is mounted upon a slidable carriage movable in a lateral and/or vertical direction so as to sequentially position a selected recess under the dispensing nozzles 113 and 123. In another embodiment, the nozzles 113 and 123, and optionally the vessels 110 and 120, are slidably movable laterally and/or vertically to accomplish positioning of the nozzles 113 and 123.

In a testing procedure, vessels 110 and 120 are filled with the selected lubricant base oil and additive(s), respectively. The apparatus of system 100 is moved such that dispensing nozzles 113 and 123 are positioned above and in alignment with recess 132a. A metered amount of base oil B and a metered amount of additive A are simultaneously dispensed into recess 132a. The dispensing nozzles 113 and 123 are thereafter repositioned to be in alignment with the next recess 132b and the metered amounts of additive A and/or base oil B are changed in accordance with a predetermined schedule of variation such that the lubricating oil in recess 132b has a different percentage composition of additive than that in recess 132a. The pattern is repeated as the nozzles 113 and 123 are sequentially aligned with the successive recesses 132c, 132d, and 132e so that each recess has a predetermined composition of lubricating oil.

The components A and B are preferably combined in the reservoirs by mixing, for example, by agitation of the frame 131, static mixing, individual stirring of the contents of the reservoirs (mechanical or magnetic stirring) and/or by bubbling the reservoir with gas, e.g., nitrogen. Optionally, base oil B and additive(s) A can be combined prior to dispensing into the respective reservoirs. For example, a single dispensing nozzle having a mixing chamber can be used, wherein base oil B and additive(s) A are metered into the mixing chamber and then dispensed through the nozzle into the reservoir.

Once the plurality of receptacles have been provided containing lubricating oil additive compositions and/or lubricating oil compositions, the plurality of fluid samples can then be analyzed, e.g., by analyzing the lubricating oil additives and lubricating oil compositions for storage stability such as, e.g., by obtaining sedimentation data, color data, and viscosity data; for oxidation stability; for antiwear properties, etc. Referring now to FIG. 2, a system for sequentially analyzing a plurality of fluid samples for storage stability is schematically illustrated. Representative of this system and method for screening the foregoing compositions in the plurality of respective test receptacles for storage stability data is one disclosed in co-pending U.S. patent application Ser. No. 10/699,505 filed on Oct. 31, 2003 and entitled "HIGH THROUGHPUT SCREENING METHODS FOR LUBRICATING OIL COMPOSITIONS" by Wollenberg et al. and having a common assignee with the present application, the contents of which are incorporated by reference herein. In general, when screening for storage stability, the samples can include lubricating oil additive compositions containing at least one lubricating oil additive or lubricating oil compositions containing one or more base oils and one or more lubricating oil additives, such as those described herein.

For example, system 200 includes means 210 for holding and optionally moving a plurality of test receptacles 212 mounted to a frame 211. In one embodiment a light source 221 is disposed on one side of frame 211 and a photocell 222 is disposed on the opposite side of frame 211 opposite, and aligned with, the light source such that a light beam emitted by the light source 221 can be detected and measured by the photocell 222. In this embodiment, photocell 222 measures the light transmitted through the sample. In another embodiment, photocell 222 is mounted so as to be aligned at a suitable angle, preferably 90°, to the incident light beam from light source 221. In this second embodiment, photocell 222 measures light scattered by the sample. The photocell converts the light received into an electrical signal, which is then transmitted via line 223 to a computer controller 230, which receives the signal as a data input. The computer controller 230 also controls movement of the samples via signal line 231 so that the samples can be sequentially moved into a position between the light source 221 and the photocell 222 upon computer command.

The samples are maintained at a predetermined temperature for a predetermined time, and optionally at a predetermined humidity, to test for storage stability as measured, for example, by the formation of sediment. The predetermined temperature can typically range from about 20° C. to about 80° C., the heat being provided by, for example, an oven in which the samples are stored or passed through. The higher temperature tends to increase the rate of instability. When utilized the predetermined humidity will ordinarily range from about 10% relative humidity to 100% relative humidity. The predetermined time is preferably at least about one day. Typically, the samples are tested every day over a period of thirty days. Longer testing times can be selected if desired, e.g., 60 days, 90 days, 365 days, etc.

In general, the samples are initially clear and transparent. Although they can be of any color ranging from, for example, light amber to dark brown, the samples initially allow for the transmission of light therethrough. Sedimentation tends to form a haze or floc, which increases the opacity or light scattering of the sample. Accordingly, a means for measuring the storage stability includes determining how much light can pass through or be scattered by the sample. In the system illustrated in FIG. 2, a light source 221 and photocell 222 are employed in a testing station 220 to accomplish this test procedure. The sample is moved into a position in testing station 220 between the light source 221 and the photocell 222, and the photocell measures how much light is transmitted through or be scattered by the sample, converts this measurement into an electrical signal, and transmits the electrical signal through line 223 to a computer controller 230. The computer controller records the signal as data which is stored and included as part of a data library, as described hereinbelow. Alternatively, the computer can convert the transmittance measurement to a Saybolt color or ASTM color value using known software to determine the storage stability of the sample, e.g., by comparing the color value to a known color range of the sample.

The computer controller preferably can also control the movement and positioning of the samples so that they can be individually tested. The test receptacles 212, for example, can be mounted to a movable carriage 211, which moves the test receptacles sequentially into a position between the light source 221 and photocell 222, as shown in FIG. 2. Alternatively, the light source 221 and photocell 222 can be moved. As yet another alternative, the samples can be grasped and individually moved by a robotic arm, as described hereinbelow.

To obtain a base line reading for comparison, the samples are initially tested for storage stability, such as by sedimentation or color measurements, prior to the step of maintaining the samples at a predetermined temperature and optionally a predetermined humidity for a predetermined time. This initial data is stored in the computer library to establish a reference point from which the subsequent storage stability data can be assessed. Preferably, just prior to taking the storage stability measurement the sample is agitated by, for example, vibrating the test receptacle, inverting the test receptacle one or more times, stirring the contents of the test receptacle, or any other suitable means in order to at least temporarily re-suspend any sediment which may have fallen to the bottom of the test receptacle. This step achieves a more uniform distribution of sediment throughout the sample, and therefore a more uniform opacity, so that the photocell does not give a false reading.

Referring now to FIG. 3, optionally, a bar code 313 can be assigned to each individual test receptacle 212 and the sample contained therein. The bar code 313 can be read by a standard bar code reader 325 at each measurement to insure that the data obtained from the sedimentation measurement corresponds to the appropriate sample. This would also facilitate changing the order of the measurement of the samples.

Figure 4:
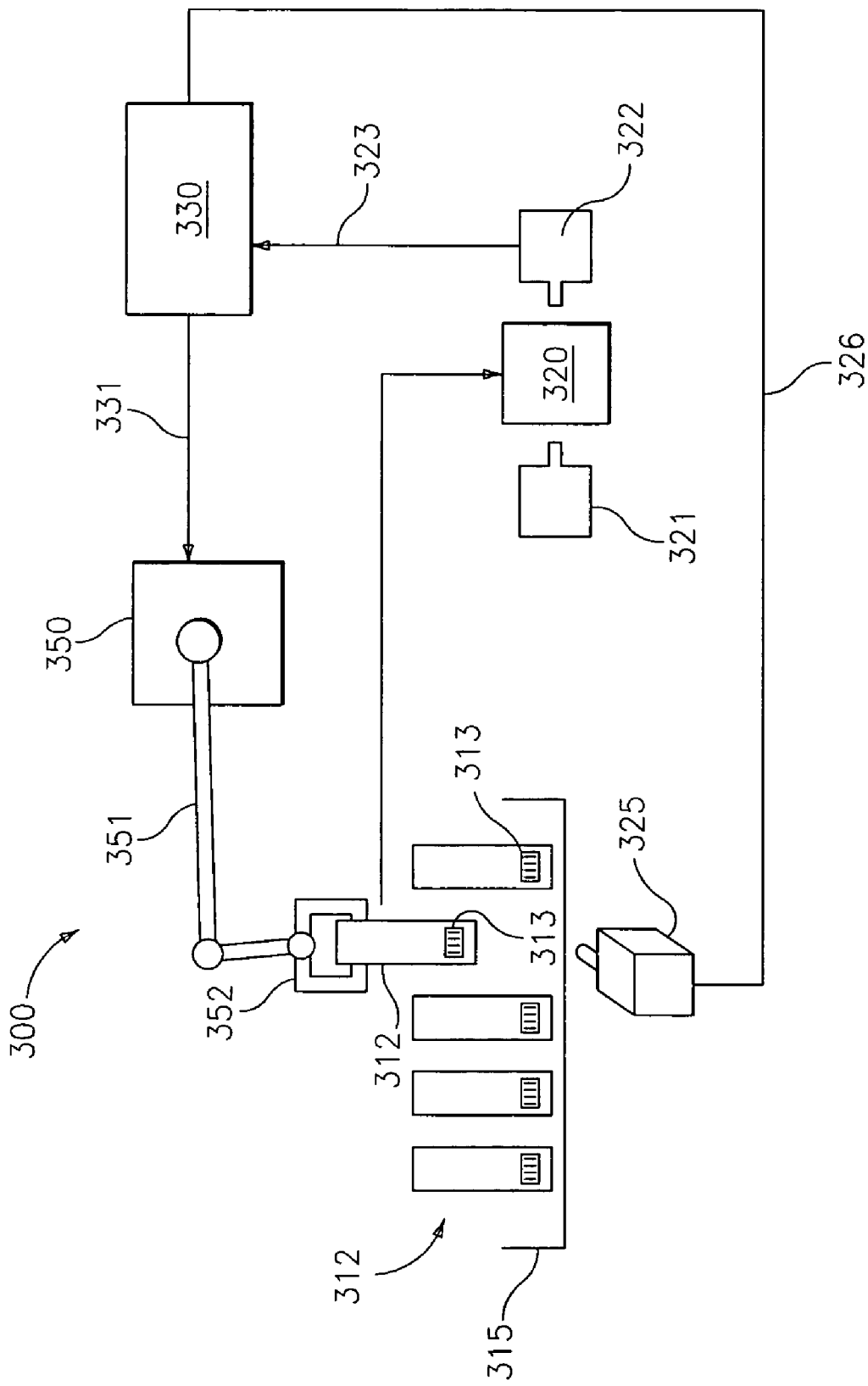

Referring now to FIG. 4, a system 300 is schematically illustrated wherein an array of test receptacles 312 are mounted in a holder 315. Each test receptacle 312 optionally includes an identifying bar code 313 affixed to the outer surface thereof. A bar code reader 325 is positioned so as to be able to read the individual bar codes of the respective test receptacles 312 and to transmit a bar code data signal to a computer controller 330 via a data transmission line 326. The bar code reader 325 is preferably movable with respect to the holder 315 so as to be positionable in alignment with selected individual test receptacles 312.

A robotic assembly 350 includes at least a movable arm 351 with a grasping mechanism 352. The robotic assembly is adapted to grasp an individual test receptacle 312 and move the test receptacle to a position in testing station 320 between the light source 321 and photocell 322 so that it can be measured for sedimentation. The robotic arm is preferably also adapted to agitate the sample in the test receptacle by, for example, by repeatedly inverting the test receptacle 312 before it is placed in position for testing. The photocell obtains a measurement of the light passage through the sample and transmits the light transmission data to the computer controller 330 through a data transmission line 323. The computer controller 330 is operatively associated with controls the robotic assembly via control signal transmission line 331 to selectively retrieve predetermined test receptacles for measurement and then replace them in their assigned respective positions in the holder 315.

In a preferred method, an assigned value of sedimentation is programmed into the computer controller for a "pass/fail" determination. The storage stability measurements are taken daily for a period of extended testing time, for example, 30 days. Those samples which fail during the course of the extended testing time are electronically marked so that they are not retested. By not retesting failed samples the system can be made to operate more efficiently, energy and time being spent only on samples which prospectively meet the desired product specifications.

Alternatively, a viscosity test may be carried out on the plurality of samples to determine storage stability. For example, an impeller (not shown) may be inserted into test receptacles 312 and initially rotated by applying a predetermined power and measuring the revolutions per minute to obtain a base line reading for comparison. Next, at predetermined time intervals the impeller is again rotated by applying the same predetermined power and measuring the revolutions per minute. When the revolutions per minute of the impeller is either higher or lower than the predetermined value of the control sample at a predetermined time, then a "pass/fail" determination can be inputted into the database.

Figure 5:
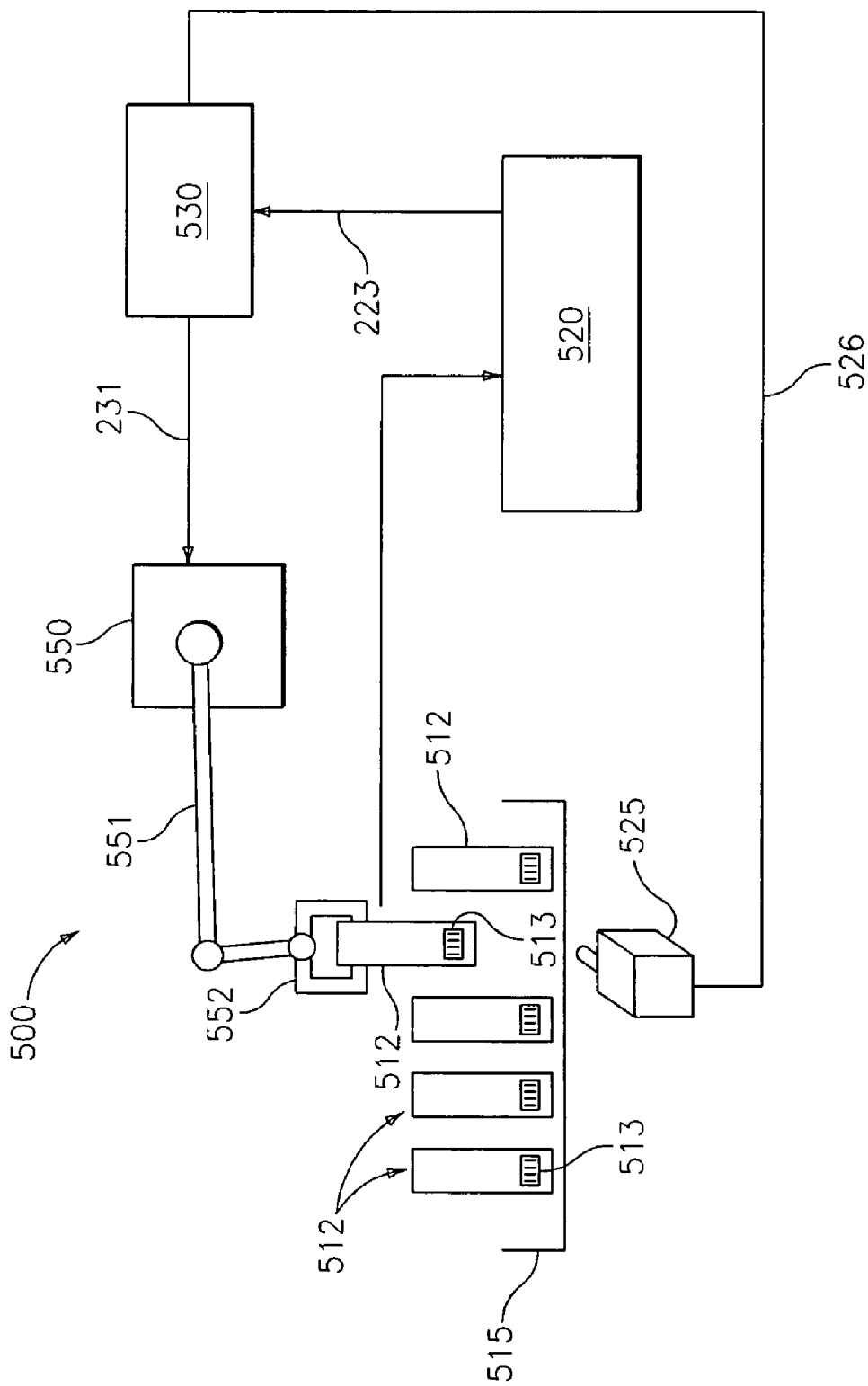
FIG. 5 is a schematic diagram of a system for high throughput oxidation screening of a variety of lubricating oil compositions.

The plurality of receptacles containing the lubricating oil compositions can also be analyzed for oxidation stability measurements such as, e.g., oxidation consumption data, deposit data, viscosity data, etc. Referring now to FIG. 5, a system for sequentially analyzing a plurality of fluid samples for antioxidant properties is schematically illustrated. Representative of this system and method for screening the foregoing compositions in the plurality of respective test receptacles for oxidation stability data is one disclosed in co-pending U.S. patent application Ser. No. 10/699,508 filed on Oct. 31, 2003 and entitled "HIGH THROUGHPUT SCREENTNG METHODS FOR LUBRICATING OIL COMPOSITIONS" by Wollenberg et al. and having a common assignee with the present application, the contents of which are incorporated by reference herein. For example, referring to FIG. 5, a system 500 is schematically illustrated wherein an array of test receptacles 512 are mounted in a holder 515. The system 500 is adapted to accommodate any number of test receptacles 212 (and samples). Each sample is identifiable, for example, by the position of its test receptacle in an ordered array in holder 515, or more preferably by having an identifying mark associated with it. For example, each test receptacle 512 can include an identifying bar code 513 affixed to the outer surface thereof. A bar code reader 525 is positioned so as to be able to read the individual bar codes of the respective test receptacles 512 and to transmit a bar code data signal to a computer controller 530 via a data transmission line 526 to electronically identify the sample. The bar code reader 525 is preferably movable with respect to the holder 515 in response to a signal from computer controller 530 so as to be positionable in alignment with selected individual test receptacles 512.

A robotic assembly 550 includes a movable arm 551 with a grasping mechanism 552. The robotic assembly is adapted to grasp an individual test receptacle 512 in accordance with selection instructions from computer controller 530 and move the test receptacle to a position in testing station 520 so that the sample in the receptacle can be measured for antioxidant properties. The computer controller 530 is operatively associated with controls to the robotic assembly via control signal transmission line 531 to selectively retrieve predetermined test receptacles for measurement and then replace them in their assigned respective positions in the holder 515.

Testing station 520 includes means for testing the samples for oxidation stability, i.e., resistance to oxidation. Oxidation stability data results of the test are converted to an electrical or optical signal and transmitted via signal transmission line 523 to computer controller 530. Various means for oxidation stability testing are known and generally include subjecting the sample to an oxygen environment and measuring the effect of oxidation upon the sample over a predetermined period of time.

For example, in one oxidation stability test method for use herein (known as the Lube Oil Oxidator test method), a sample of oil is weighed into an oxidator cell, e.g., glass. A glass stirrer is inserted into the cell, and the cell is sealed. Typically, the stirrer is magnetically coupled to a stir motor which is external to the oxidator cell. To an area above the oil sample can be placed a sufficient solid material suitable for absorption of carbon dioxide gas which may be liberated during oxidation of the test lube oil, e.g., potassium hydroxide. Optionally, a catalyst may be added to the lube oil to assist in accelerating oxidation and is chosen to simulate the types of metal ions typically found in an internal combustion engine.

The cell is then placed in an oil bath maintained at a predetermined temperature, e.g., a temperature ranging from about 250° F. to about 400° F. and preferably from about 300° F. to about 350° F., and connected to an oxygen supply. A sufficient quantity of oxygen is fed into the cell while the stirrer agitates the oil sample. The test is run until the quantity of oxygen is consumed by the sample and the total time, e.g., in hours, of the sample run is reported. In general, large scale operation typically requires one liter of oxygen for a 25 gram sample. Accordingly, smaller quantities of sample require proportionately smaller volumes of oxygen and are within the purview of one skilled in the art. If desired, results from measurements of the current quantity of oxygen that is consumed as well as the lube oil viscosity can be recorded at predetermined time intervals to a computer database for later analysis. In a variation of this test, the amount of oxygen consumed after a predetermined time period, e.g., about a 10 hour test, is measured while recording to a computer database at time intervals the volume of oxygen uptake and the lube oil viscosity. Suitable high throughput methods for measuring viscosity are disclosed in EP 1158290, WO 99/18431, U.S. 2003/0037601, U.S. Pat. No. 6,383,898, and WO 03/019150.

Another oxidation stability test method for use herein is one which determines the temperature where a test oil undergoes oxidation and deposit formation on, for example, a transparent tube. In this method, the transparent glass tube can be placed inside a metal heating block, e.g., an aluminum heating block, and a small air hose is attached to a holder at the bottom of the glass tube. Next, a suitable nozzle, e.g., about a 5 ml syringe, and a suitable hose, e.g., about a 12 inch flexible tubing, are filled with the oil sample.

The tubing is attached to a holder on the glass tube above the air hose and oil is steadily introduced into the glass tube by the nozzle. Air forces the test oil up the glass tube through the heating block for the duration of the test. The rates of air flow and sample introduction are controlled such that the entire sample is injected within a predetermined time, e.g., a 16 hour time period. The oxidation of the oil gradually forms a dark deposit on the inner wall of the glass tube. The heating block is temperature controlled within small limits and the test conditions are generally chosen over a range of temperatures, e.g., from about 230° C. to about 330° C., and tests can be run at different temperatures to determine deposit formation over a temperature range. After a predetermined period of time (e.g., 16 hours) the glass tube is removed from the test apparatus, rinsed with a suitable solvent, and the amount of deposit is measured in accordance with the darkness of the deposit in the tube, the darkness indicating the quantity of the deposit and the amount of oxidation. The measurement is compared against a predetermined standard set of tubes.

While the determination of the deposit formation can be performed manually by visually inspecting the test tube, comparing it with the standard set of tubes, and estimating the degree of deposit formation, the present method is automated and preferably employs a light source and a photocell. The amount of deposit can be measured by directing a beam of light from the light source through the tube and measuring the amount of light transmitted through the tube by means of the photocell. The opacity of the tube indicates the amount of deposit, and hence, the amount of oxidation of the sample.

Figure 6:
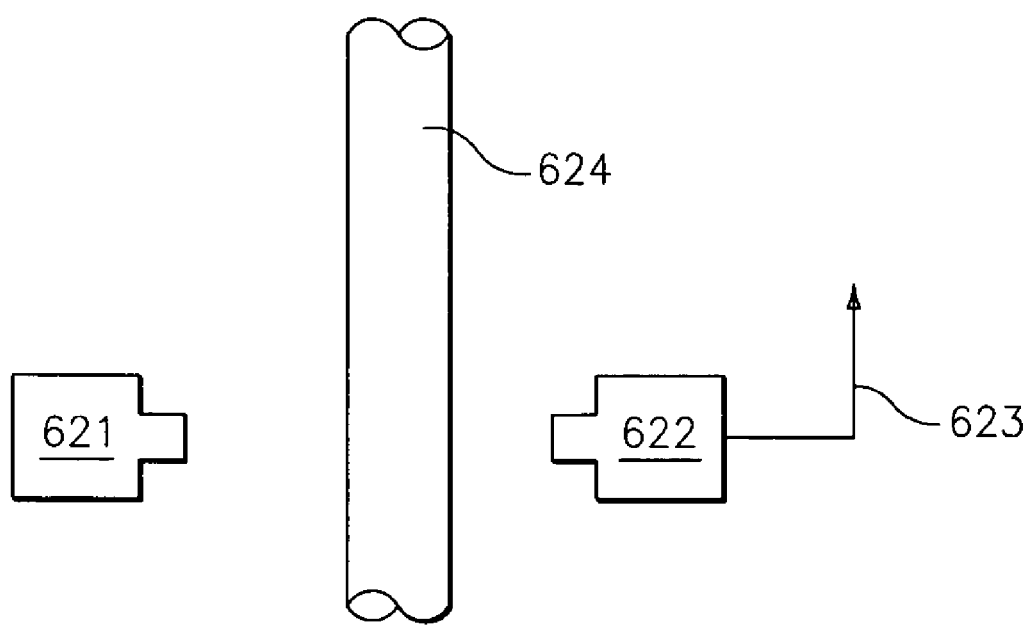
FIG. 6 is a schematic diagram of a photocell system for measuring deposit formation on a substrate.

For example, referring to FIG. 6, test tube 624 from a Komatsu Hot Tube testing apparatus is positioned between light source 621 and photocell 622. A beam of light from the light source is directed through the test tube 624 and is measured by the photocell 622, which measures the amount of transmitted light, converts this reading to an electrical signal, and transmits the signal via line 623 to the computer controller 630. The computer controller 630 has stored values of light transmittance (or opacity) for the standard set of tubes and rates the oxidation value of the test sample by comparison with the standard set. The oxidation rating is assigned to the test sample (which can be identified by the bar code) and the information is stored as a component of the data library. The computer controller can thereafter modify the selection instructions. Programming to accomplish the various functions of the computer controller 630 are within the purview of those with skill in the art.

In another oxidation stability test method for use herein, each of the foregoing samples can be placed in an oxidation container and maintained at a predetermined temperature for a predetermined time. The oxidation container can be a material which is suitable for infrared transmittance, e.g., borosilicate glass. The predetermined temperature can ordinarily range from about 100° C. to about 200° C. and preferably from about 140° C. to about 180° C. The predetermined time may vary up to about 40 hours. Additionally, air is bubbled into the test oil at a constant rate of flow and in the presence of a metallic oxidation catalyst, e.g., a combination of metal ions such as copper, lead and aluminum. The air flow rate can be determined by one skilled in the art (e.g., 13.9 L/hr±0.5 L/hr has been used for a 200-g sample of test oil). The degree of oxidation is then determined by measuring the infrared absorbance of the carbonyl peak at 1710 $cm^{-1}$ using, e.g., a Fourier transform infrared spectrometer (e.g. a Bruker IFS 48 infrared apparatus). As oxidation takes place, the absorbance peak at 1710 $cm^{-1}$ increases owing to oxidation of the test oil as carbonyl-containing functional groups are produced. The data is then recorded in a computer database. A suitable high-throughput method for measuring infrared absorbance is taught in U.S. Patent Application No. 2002/0197731.

Another oxidation stability test method for use in the present invention utilizes differential scanning calorimetry. In general, differential scanning calorimetry is a technique to measure oxidation stability of a test oil sample as it is heated. In this method, the sample is placed in a suitable vessel, e.g., a 10-mL air-tight vial, and held at a predetermined temperature, e.g., from about 120° C. to about 200° C., by using a heating source, e.g., an oven. Automated computer data collection occurs throughout the experiment with individual data points representing temperature and heat flow between the sample and reference and each time of measurement being recorded. Accordingly, an objective of this test is to measure the thermal stability of an oil sample at a predetermined temperature in air-tight model systems to determine the exothermic release of heat. The temperature at which the exothermic release of heat is observed is called the oxidation onset temperature and is a measure of the oxidative stability of the oil.

In an alternative embodiment of an oxidation stability test method for use in the present invention (known as the thin film oxygen uptake test (TFOUT) method, e.g., ASTM D 4742), a sample of oil is weighed into a TFOUT glass dish together with a suitable amount of a fuel fraction sample, liquid metal catalyst, and water sample. The sample is placed in a suitable container, e.g., a steel bomb, and charged with a predetermined amount of oxygen, e.g., from about 30 psi to about 90 psi, at room temperature. The container is then submerged in an oil bath maintained at a predetermined temperature, e.g., 120° C. to about 200° C., and rotated at a predetermined speed, e.g., about 50 rpm to about 140 rpm. A chart recorder can constantly monitors the oxygen pressure and when there is a rapid pressure drop the test is over. The time from the start of the test to the rapid pressure drop is recorded. If the time is above or below a predetermined value, the sample is assigned a pass/fail determination.

If desired, an assigned value of oxidation is programmed into the computer controller for "pass/fail" determination. Assigned pass/fail values can be selected based upon performance requirements for specific lubricant applications and prospective operating environments. If the test sample fails by having an excessively high oxidation value, the test sample can be electronically marked and future testing of lubricant oil formulations having the same composition as the sample can be eliminated from further testing for other performance characteristics. By not retesting failed samples the system can be made to operate more efficiently, energy and time being spent only on samples which prospectively meet the desired product specifications.

If desired the results of the methods of the present invention can be monitored from a remote location, i.e., a location which is not in direct or at least in visual contact with the system operating the method of the invention. A remote location can be, for example, a central process control system or room which, as part of the overall system for use herein, monitors and controls the system as well as records the outputs of each of the results of the tests being carried out. In this way, it becomes possible for less interaction with personnel being stationed at the location of the system. Suitable data lines, with which the results of the output, as well as control commands, may be transmitted, are known.

The plurality of receptacles containing the lubricating oil compositions can also be analyzed for respective anti-wear properties, i.e., wear stability. While classification of wear types includes, but are not limited to, adhesive wear, abrasive wear, fatigue, and polishing, the following are generally three major wear tests: extreme-pressure wear tests, hydrodynamic wear tests and corrosive wear tests. Representative of a system and method for screening the foregoing compositions in the plurality of respective test receptacles for antiwear data is one disclosed in co-pending U.S. patent application Ser. No. 10/699,509 filed on Oct. 31,2003 and entitled "HIGH THROUGHPUT SCREENING METHODS FOR LUBRICATING OIL COMPOSITIONS" by Wollenberg et. al. and having a common assignee with the present application, the contents of which are incorporated by reference herein.

An extreme-pressure wear test is associated with a situation where the lubricating oil composition has been squeezed out of, for example, an engine, leaving only a non-fluid film of anti-wear additive of the tested composition that has been chemically bonded to the interacting engine surfaces. For example, an extreme wear condition occurs between the piston ring and cylinder wall in a running internal combustion engine when the piston reaches the upper dead center and is subjected to the force of the fuel combustion explosion while the piston is for an instant not in sliding motion.

A hydrodynamic test is designed to test the ability of the lubricating oil compositions to prevent wear under conditions wherein a fluid lubricant film is retained between the interacting surfaces. Typically, a hydrodynamic lubricant condition occurs in an internal combustion engine between the piston rings and cylinder wall when the piston is in sliding motion during the stroke.

Finally, a corrosive wear test is designed to test the ability of the lubricating oil composition to protect the interacting surfaces from wear in a corrosive environment. The latter may be observed in an internal combustion engine due to the oxidation of components in the fuel to be combusted or in the lubricating oil composition, e.g., in the case where sulfur generates sulfuric acid.

Figure 7:
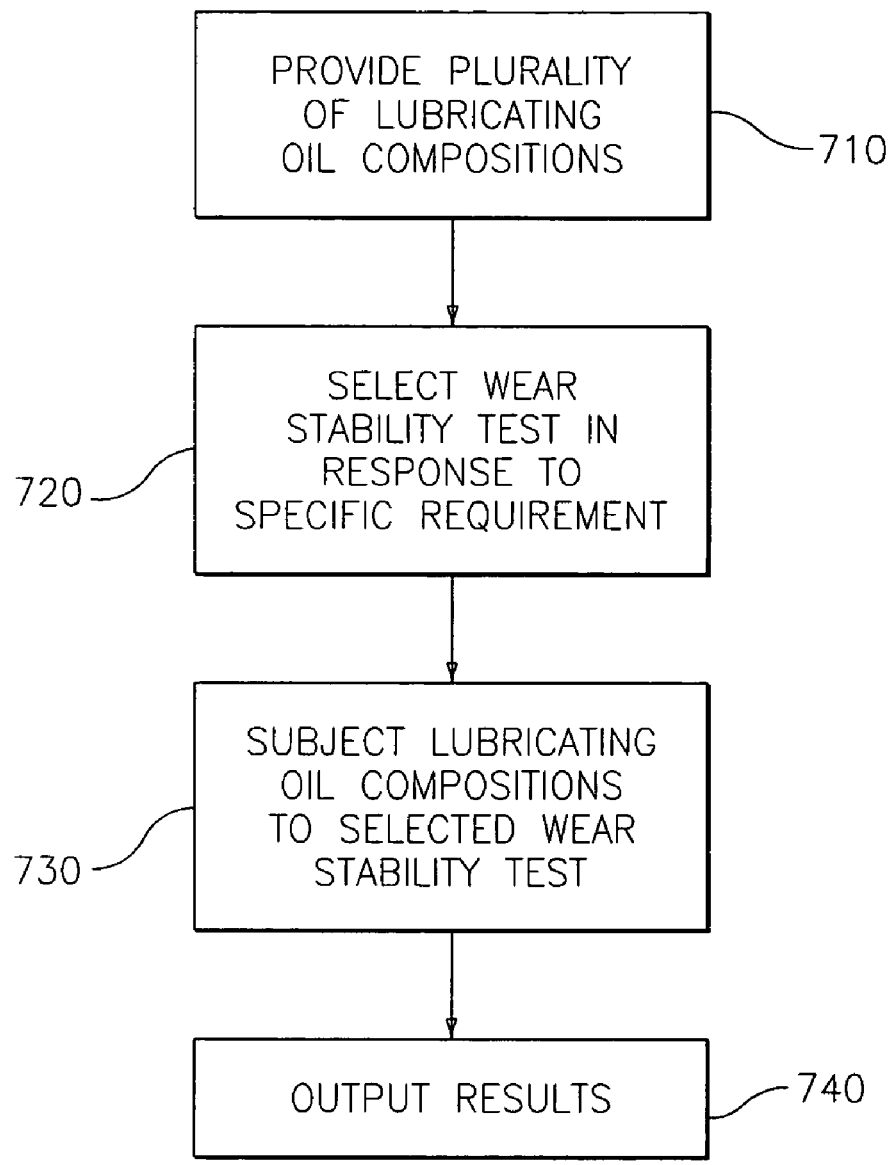
FIG. 7 is a flow chart for determining and storing anti-wear properties of a plurality of lubricating oil compositions provided in accordance with the system of FIG. 1.
Figure 8:
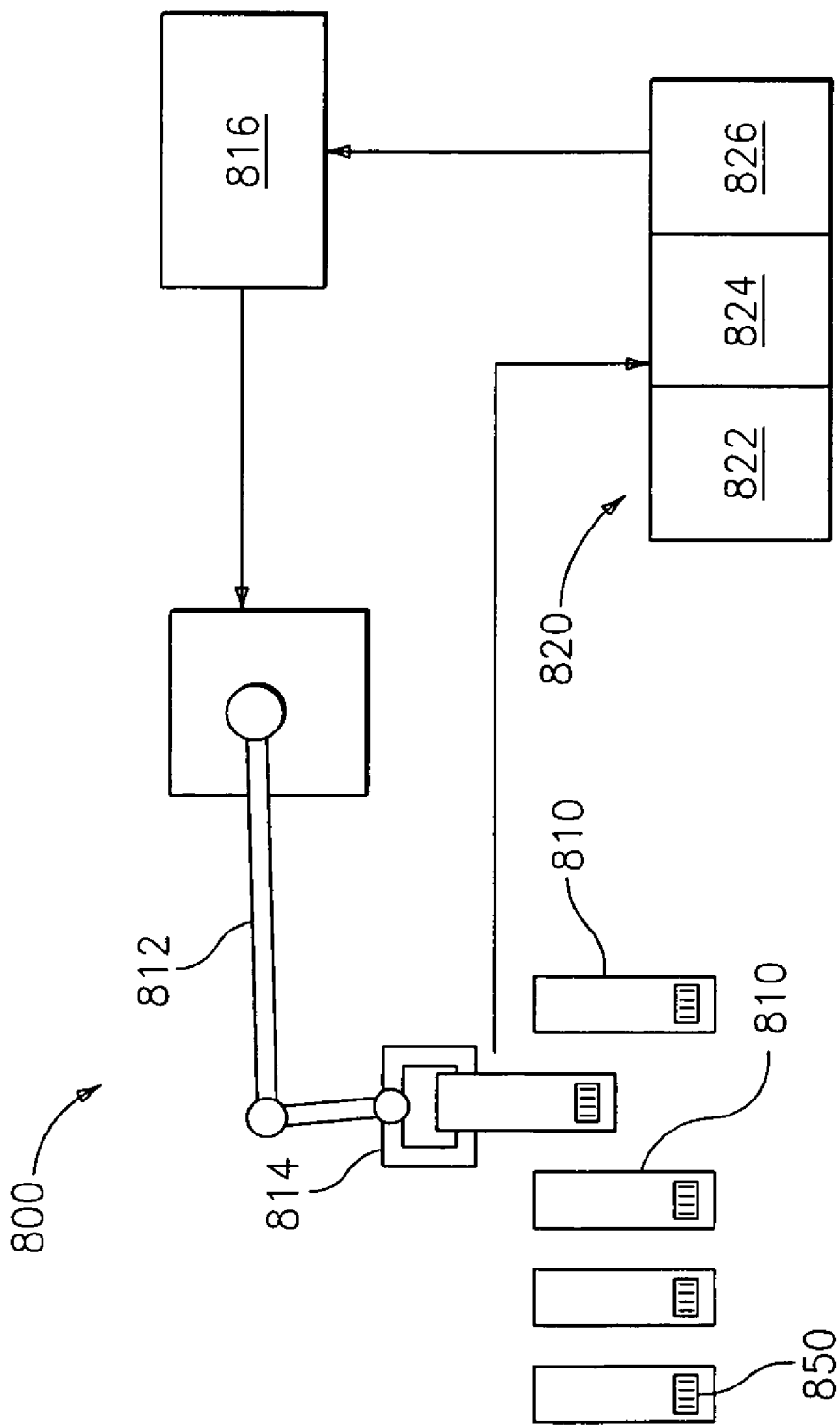
FIG. 8 is a diagrammatic view of an example of the system of the present invention capable of carrying out the method of FIG. 7.

Referring now to FIGS. 7 and 8, the method and system of the present invention for sequentially analyzing anti-wear properties of a plurality of lubricating oil compositions, stored in the library in accordance with FIG. 1, are illustrated. Adding the information related to the anti-wear properties of each of the stored lubricating oil compositions substantially facilitates the selection of candidate compositions capable of successfully carrying out the extreme-pressure, hydrodynamic and corrosive wear stability tests under the desired operating conditions or statutory requirements.

Having provided a plurality of lubricating oil compositions at 710 (FIG. 7), a robotic assembly 800 (FIG. 8) is adapted to carry out each of the tests by selectively delivering test receptacles 810, each containing a respective sample identifying code bar 850, to a testing station 820. The robotic assembly is configured to have one or more movable arms 812 each provided with a grasping mechanism 814, which engages the individual test receptacles 810 in accordance with instructions from a computer controller 816.

The testing station 820 may include a single testing apparatus performing one test at a time, or preferably, this station is assembled of multiple apparatuses operating simultaneously so that each carries out a respective test in accordance with instructions 720 (FIG. 7) from the controller 816. In the case of multiple apparatuses, a tested lubricating oil composition can be distributed among an extreme pressure test apparatus 822, hydrodynamic test apparatus 834 and a corrosive test apparatus 826 or multiple identical lubricating oil compositions may be separately tested in any of the forgoing test apparatuses. Each of the test apparatuses operates under the desired and controlled conditions including, among others, a predetermined temperature, load and acid concentration corresponding to those specified in existing or proposed statutory requirements and corresponding to multiple parts of or the entire running engine. Thus, for example, the extreme pressure test apparatus 822 may operate so that the applied load sequentially increases in a time controlled manner from, for example, about 200 lbs. to about 300 lbs. to about 400 lbs. The hydrodynamic test apparatus 824 may be controlled to increase the load from, for example, about 50 lbs. to about 100 lbs. to about 150 lbs at intervals identical to or different from the intervals associated with the load increase in the extreme load apparatus 824. Finally, a corrosive element such as, for example, sulfuric acid, can be delivered in computer-controlled concentrations to the corrosive test apparatus 826 to recreate the desired corrosive environment corresponding to predetermined loads and acid concentrations to determine the corrosive wear stability of the lubricating oil composition. It is to be understood that the specific load and acid concentration conditions are not the only parameters that can be controllably created and modified in association with each of the test apparatuses.

As each of the lubricating oil compositions or a subset thereof is subjected to the foregoing test(s), as indicated by 730 of FIG. 7, the computer controller 816 (FIG. 7) processes and outputs respective test results at 740, each of which is added to the library. Accordingly, the information regarding the anti-wear properties of lubricating oil compositions stored in the library becomes another piece of information in addition to, for example, storage stability and oxidation stability of the cataloged compositions.

Figure 9:
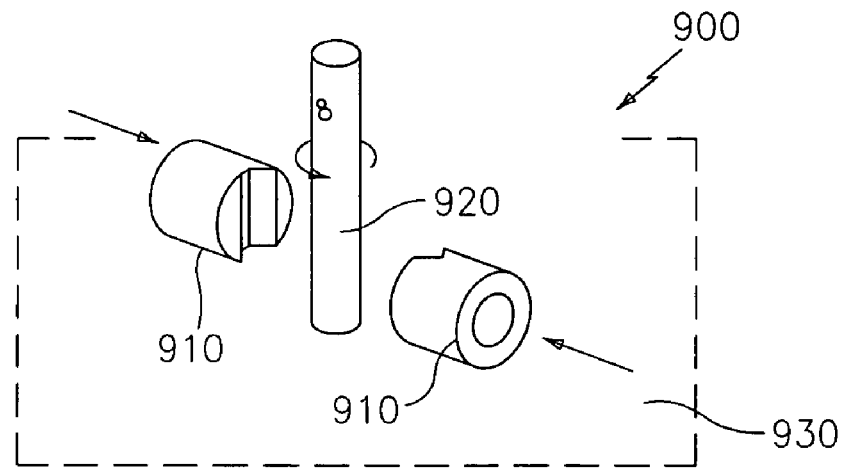
FIG. 9 is an exploded view of a Test Pin and Vee Block shown as an example of machinery capable of carrying out a plurality of wear tests in accordance with the method and system of the present invention; and, FIG. 10 is an isometric view of Four-Ball Block Test 800 shown as another example of machinery capable of carrying out a plurality of wear tests in accordance with the method and system of the present invention.
Figure 10:
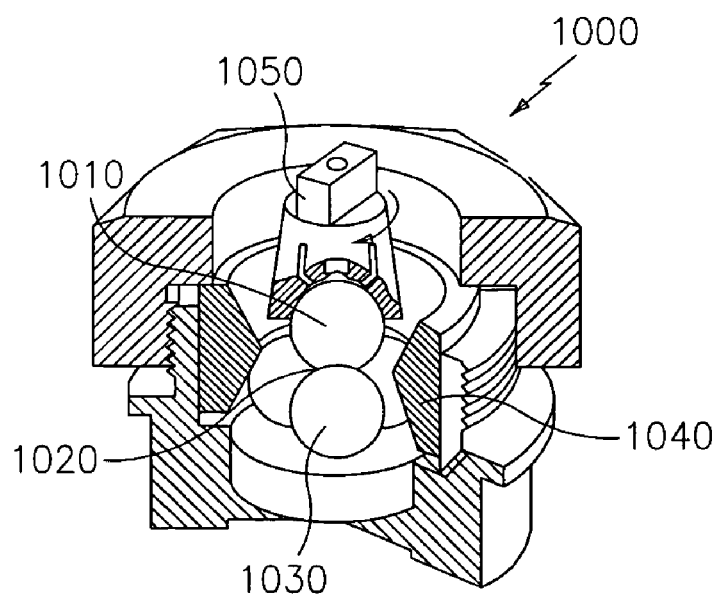

A variety of lubricant and wear testing machines or apparatuses are known to carry out the above-discussed tests. For example, as illustrated in FIGS. 9 and 10, Test Pin and Vee Block 900 and Four-Ball Test 1000 assemblies, respectively, each are capable of performing the extreme pressure, hydrodynamic and corrosive wear tests either individually or in combination. For example, in the Test Pin configuration of FIG. 9, two Vee Blocks 910 can be controllably pressed against a rotating journal 920, which is submerged in a cup 930 with the tested lubricating oil composition. Accordingly, the hydrodynamic and extreme pressure tests for each of the lubricating oil compositions can be conducted sequentially by controllably increasing load. The corrosive test can be carried out simultaneously with or separately from each of the former two tests by delivering measured concentrations of an oxidation medium to the journal. Such delivery can be realized, for instance, by constantly injecting sulfuric acid at the point of the journal. Of course, the wear and/or rate of wear increases as the acid concentration increases.

The four-ball test configuration 1000, as shown in FIG. 10, is constructed so that the three bottom test balls 1030 are placed in a stationary holder 1040, locked in place, and covered with a respective one of the lubricating oil compositions 1020. Upon placing a top ball 1010 in a chuck and attaching the top ball 1010 to a spindle 1050, the load is applied in a computer-controlled manner, as discussed above. Depending on which of the hydrodynamic and extreme pressure tests is being run, it is possible to determine either the load wear index corresponding to the scar diameter from the tests run or the weld point.

If desired, the results of the data obtained can be monitored from a remote location, i.e., a location which is not in direct or at least in visual contact with the system operating the method of the invention. A remote location can be, for example, a central process control system or room which, as part of the overall system for use herein, monitors and controls the system as well as records the outputs of each of the results of the tests being carried out. In this way, it becomes possible for less interaction with personnel being stationed at the location of the system. Suitable data lines, with which the results of the output, as well as control commands, may be transmitted, are known.

Also, the storage stability data, oxidation data and antiwear data regarding the lubricating oil additive or lubricating oil compositions can be stored in a relational database to provide a combinatorial lubricating oil composition library of the present invention. Alternatively, the system may be electrically connected to a signal data collector comprising a computer microprocessor for system operation and control to collect the data from the various tests over an extended period of time to compile the combinatorial lubricating oil composition library. The database can be used to find optimum combinations for a desired product stream, and can be particularly useful when the desired product stream varies depending on market factors. When the product requirements change, appropriate combinations can be selected to prepare the desired product.

Relational database software can be used to correlate the identity of the additive(s) and lubricating oil compositions and the analytical storage stability data obtained therefrom. Numerous commercially available relational database software programs are available, for example, from Oracle, Tripos, MDL, Oxford Molecular ("Chemical Design"), IDBS ("Activity Base"), and other software vendors.

Relational database software is a preferred type of software for managing the data obtained during the methods described herein. However, any software that is able to create a "memory map" of the lubricating oil additive and lubricating oil compositions and correlate that information with the information obtained from the storage stability measurements can be used. This type of software is well known to those of skill in the art.

What is claimed is:

1. A combinatorial lubricating oil composition library comprising (i) a plurality of different lubricating oil compositions comprising (a) a major amount of at least one base oil of lubricating viscosity and (b) a minor amount of at least one lubricating oil additive, wherein the plurality of different lubricating oil compositions is at least 20, and (ii) lubricating oil composition property data for each of the plurality of different lubricating oil compositions and further wherein the lubricating oil composition property data is derived from conditions associated with an engine test.

2. The combinatorial lubricating oil composition library of claim 1, wherein the lubricating oil composition property data is antiwear data derived from an extreme wear condition associated with an extreme wear pressure test occurring between a piston ring and cylinder wall in a running internal combustion engine when a piston reaches an upper dead center and is subjected to a force of fuel combustion explosion while the piston is for an instant not in sliding motion.

3. The combinatorial lubricating oil composition library of claim 2, wherein the at least one lubricating oil additive is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

4. The combinatorial lubricating oil composition library of claim 1, wherein the lubricating oil composition property data is antiwear data derived from a hydrodynamic lubricant condition associated with a hydrodynamic wear test occurring in an internal combustion engine between piston rings and a cylinder wall when a piston is in sliding motion during a stroke.

5. The combinatorial lubricating oil composition library of claim 4, wherein the at least one lubricating oil additive is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

6. The combinatorial lubricating oil composition library of claim 1, wherein the at least one base oil is selected from the group consisting of engine oils, transmission fluids, hydraulic fluids, gear oils, marine cylinder oils, compressor oils, refrigeration lubricants and mixtures thereof.

7. The combinatorial lubricating oil composition library of claim 1, wherein the at least one base oil has a viscosity of about 2 to about 2000 centistokes (cSt) at 100° C.

8. The combinatorial lubricating oil composition library of claim 1, wherein the at least one base oil has a kinematic viscosity of about 2 cSt to about 30 cSt at 100° C.

9. The combinatorial lubricating oil composition library of claim 1, wherein the at least one base oil has a kinematic viscosity of about 3 cSt to about 16 cSt at 100° C.

10. The combinatorial lubricating oil composition library of claim 1, wherein the at least one base oil has a kinematic viscosity of about 4 cSt to about 12 cSt at 100° C.

11. The combinatorial lubricating oil composition library of claim 1, wherein the at least one base oil has a SAB Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20 , 15W-30 or 15W-40.

12. The combinatorial lubricating oil composition library of claim 1, wherein the at least one base oil is a natural or synthetic oil.

13. The combinatorial lubricating oil composition library of claim 1, wherein the at least one lubricating oil additive is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

14. The combinatorial lubricating oil composition library of claim 1, wherein the lubricating oil composition property data is selected from the group consisting of oxidation stability data, antiwear data and mixtures thereof.

15. The combinatorial lubricating oil composition library of claim 1, wherein the plurality of different lubricating oil compositions is at least 100.

16. A high throughput method for producing a combinatorial lubricating oil composition library, under program control, comprising
(a) providing a library of a vast number of a plurality of different lubricating oil composition samples comprising (i) a major amount of at least one base oil of lubricating viscosity and (ii) a minor amount of at least one lubricating oil additive, each sample being in a respective one of a plurality of test receptacles, wherein the plurality of different lubricating oil compositions is at least 20;
(b) measuring lubricating oil composition properties of each sample to provide lubricating oil composition property data for each sample, wherein the lubricating oil composition property data is derived from conditions associated with an engine test; and,
(c) outputting the results of step (b).

17. The method of claim 16, wherein the at least one base oil is selected from the group consisting of engine oils, transmission fluids, hydraulic fluids, gear oils, marine cylinder oils, compressor oils, refrigeration lubricants and mixtures thereof.

18. The method of claim 16, wherein the at least one base oil is a natural or synthetic oil.

19. The method of claim 16, wherein the at least one lubricating oil additive is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

20. The method of claim 16, wherein measuring step (b) comprises an oxidation stability measurement, or antiwear measurement.

21. The method of claim 16, wherein in step (c) the result of step (b) for each sample is transmitted to a computer, the computer compares the result with a predetermined value delimiting a failure or passing of the result, and the computer identifies failed samples to preclude further testing of the failed samples.

22. The method of claim 16, wherein the step (c) of outputting comprises storing the results of step (b) on a data carrier.

23. The method of claim 22, further comprising the step of transmitting the result of step (b) to a remote location.

24. The method of claim 16, further comprising the step of using the results of step (b) as a basis for obtaining a result of further calculations.

25. The method of claim 24, further comprising the step of transmitting the result of further calculations to a remote location.

* * * * *